United States Patent [19]

Fletcher

[11] Patent Number: 4,460,694

[45] Date of Patent: Jul. 17, 1984

[54] BOVINE GLYCOPROTEINS AND USE IN DIAGNOSING INFECTIOUS MONONUCLEOSIS

[75] Inventor: Mary A. Fletcher, Miami, Fla.

[73] Assignee: University of Miami, Coral Gables, Fla.

[21] Appl. No.: 356,348

[22] Filed: Mar. 9, 1982

Related U.S. Application Data

[63] Continuation-in-part of Ser. No. 247,934, Mar. 26, 1981.

[51] Int. Cl.$^3$ .................... G01N 33/54; G01N 33/56; C07G 7/00
[52] U.S. Cl. .................................. 436/531; 436/534; 436/542; 436/800; 436/804; 436/812; 260/112 B; 435/7
[58] Field of Search .................. 424/41.5; 260/112 R, 260/112 B; 436/531, 534, 542, 800, 804, 812; 435/7

[56] References Cited

U.S. PATENT DOCUMENTS

| | | |
|---|---|---|
| 3,426,123 | 2/1969 | Hoff . |
| 3,639,558 | 2/1972 | Catzmas et al. . |
| 3,708,572 | 1/1973 | Petoom et al. . |
| 3,826,821 | 7/1974 | Zichis . |
| 3,840,655 | 10/1974 | Lerner . |
| 3,857,931 | 12/1974 | Hager . |
| 3,864,467 | 2/1975 | Leikolin . |
| 3,882,225 | 5/1975 | Patel et al. . |
| 3,959,456 | 5/1976 | Zichis . |
| 4,046,723 | 9/1977 | Dorman . |
| 4,228,148 | 10/1980 | Zichis et al. . |

OTHER PUBLICATIONS

Merrick et al., Chem. Abstracts, vol. 87, (1977), abstract #198965f.
Fletcher, J. Immunol., vol. 117, (1976); 722-729.
Fletcher et al., Chem. Abstracts, vol. 81, (1974), Abstract #76159b.
Fletcher et al., Chem. Abstracts, vol. 87, (1977), Abstract #49104x.
Callahan, Chem. Abstracts, vol. 86, (1977), Abstract #3370g.
Marchesi, V. T. et al. *Ann. Rev. Biochem.* 45, 667 (1976), The Red Cell Membrane.
Paul, J. R. et al. *Amer. J. Med. Sci.* 183, 90 (1932), The Presence of Heterophile Antibodies in Infectious Mononucleosis.
Davidsohn, I. et al. *Amer. J. Clin. Pathol.* 5, 455 (1935), The Nature of Heterophilic Antibodies in Infectious Mononucleosis.
Bailey, G. H. et al. *J. Clin. Invest.* 14,228 (1935), Hemolytic Antibodies for Sheep and Ox Erythrocytes in Infectious Mononucleosis.
Evans, A. S. et al. *J. Infect. Dis.* 132,546 (1975), A Prospective Evaluation of Heterophile and EB Virus-specific IgM Antibody Tests.
Fletcher, M. A. et al. *J. Immunol.* 107,842 (1971), Immunochemical Studies of Infectious Mononucleosis.
Levey, B. A. et al. *J. Clin. Microbio.* 11,256 (1980), Latex Test for Serodiagnosis of Infectious Mononucleosis.
Lee, C. L. et al. *Amer. J. Clin. Pathol.* 49,12 (1968), Horse Agglutinins in Infectious Mononucleosis.
Editorial, *Brit. Med. J.* 280,1153 (1980), Tests for Infectious Mononucleosis.
Fraker, P. J. et al. *Biochem. Biophys. Res. Commun.* 80,849 (1978), Protein & Cell Membrane Iodinations with a Sparingly Soluble Chloramide.
Svennerholm, L. *Biochem. Biophys. Acta* 24,604 (1957), Quantitative Estimation of Sialic Acids.
Fletcher, M. A. et al. *J. Immunol. Methods.* 14,51 (1977), Immunochemical Studies of Infectious Mononucleosis.
Dejter-Juszynski, M. et al. *Eur. J. Biochem.* 83,363 (1978), Blood-Group ABH-Specific Macroglycolipids of Human Erythrocytes: Isolation in High Yield from a Crude Membrane Glycoprotein Fraction.

*Primary Examiner*—Christine M. Nucker
*Attorney, Agent, or Firm*—Irons and Sears

[57] ABSTRACT

A novel purification scheme is described for obtaining two novel and useful forms of bovine glycoprotein (BGP) from bovine erythrocytes, each of which acts as an antigen in testing for the presence of the heterophile antibodies of human infectious mononucleosis.

The first, or partially purified, BGP is obtained from crude BGP and contains about 10% by weight of a complex glycoplipid. It forms a single band upon gel electrophoresis at pH 7.0 under specified conditions.

The second, or homogeneous, BGP is obtained by removing essentially all of the complex glycolipid. It forms substantially a single band upon gel electrophoresis at pH 7.0 under specified conditions.

Both forms may be used to detect or quantify hemagglutination inhibition of a test sample (and hence to determine the presence or extent to mononucleosis infection) in a glass slide test wherein the partially purified or homogeneous BGP is carried on latex or synthetic resin beads.

The homogeneous BGP is also useful in an immunoassay, preferably a radioimmunoassay, for heterophile antibodies characteristic of infectious mononucleosis.

25 Claims, No Drawings

BOVINE GLYCOPROTEINS AND USE IN DIAGNOSING INFECTIOUS MONONUCLEOSIS

This application is a continuation-in-part of application Ser. No. 247,934, filed Mar. 26, 1981.

INTRODUCTION

This invention pertains to new and useful methods for diagnosing and monitoring the course of infectious mononucleosis, and to a new bovine antigen in two different glycoprotein forms, each highly purified. A multi-step process for purification of the bovine antigen is also encompassed. More particularly, the invention involves using either form of the new antigen in slide tests, and the purer of the two forms in immunoassays, especially radioimmunoassays, for detecting and for quantifying infectious mononucleosis (IM) antibodies.

BACKGROUND OF THE INVENTION

Attempts at immunological diagnosis or monitoring of the course of infectious mononucleosis have heretofore emphasized the use of whole erythrocyte fractions. Erythrocytes are known to contain many different membrane proteins, each of which may be reactive with one or more different antibodies [Marchesi, V. T., H. Furthmayr and M. Tomita, *Ann. Rev. Biochem.* 45, 667–698 (1976)]. Because whole erythrocytes, or crude erythrocyte fractions, may be agglutinated by antibodies of widely varying characteristics, including many that are unrelated to IM, false positives have been a problem. Avoidance of false positives is clearly important to effective and reliable clinical diagnosis. This invention, in its preferred form, involves a homogeneous bovine glycoprotein (hereinafter BGP) which, by virtue of its homogenity, has greater specificity and sensitivity to IM antibodies.

Immunological diagnosis of infectious mononucleosis was first reported in 1932 by Paul and Bunnell in *Amer. J. Med. Sci.* 183, 90–104 (1932). They taught that red blood cells or erythrocytes, from species such as sheep can be agglutinated by IM heterophile antibodies contained in serum from patients with active infectious mononucleosis. Many assays that detect these heterophile antibodies were subsequently developed, see e.g., U.S. Pat. Nos. 3,426,123 and 3,708,572.

It was meanwhile reported that preincubation of the patient's serum with guinea pig kidney absorbed or precipitated out the so-called Forssman antibody, a ubiquitous antibody that interferes with the detection of the heterophile antibodies [Davidsohn, I. & P. H. Walker, *Amer. J. Clin. Pathol.* 5, 455–465 (1935)]. Absorption or preincubation of IM serum with guinea pig kidney increased the specificity of the agglutination assay, but required an absorption step before the agglutination reaction was initiated (see, for example, U.S. Pat. Nos. 3,959,456 and 3,864,467).

Bovine erythrocytes were ultimately found to be specific in detecting IM heterophile antibodies. In the early work on red blood cells of this species, Bailey and Raffel [*J. Clin. Invest.* 14, 228–244 (1935)] found that native bovine erythrocytes were not agglutinated by serum containing IM antibodies, but that these erythrocytes did absorb the heterophile antibody and were lysed in the presence of complement. This bovine erythrocyte hemolysin test was later reported to be more specific for heterophile antibody than agglutination tests using horse or sheep erythrocytes, even when a preabsorption step with guinea pig kidney was utilized. [Evans, A. S. et al., *J. Infect. Dis.* 132, 546–554 (1975)]. Evans et al., suggested that bovine erythrocytes contain immunological determinant(s) which bind more specifically to heterophile antibodies than the immunological determinants present in erythrocytes from other species, such as goat, sheet or horse.

In summary, the most widely used tests to date for the diagnosis of infectious mononucleosis involve either agglutination or complement-mediated hemolysis of red blood cells from human sources. The more specific of these has been hemolysis with bovine red blood cells. The bovine erythrocyte hemolysin test, however, is impractical because cell lysis with complement is difficult to reproduce. The results may vary from batch to batch of bovine red blood cells and from sample to sample of complement. Agglutination of other erythrocytes is far from completely satisfactory because of the need for time-consuming pre-adsorption of serum with guinea pig kidney tissue. Furthermore, both methods may give false positives.

As early as 1971, the present inventor and coworkers [Fletcher, M. A. & B. J. Woolfolk, *J. Immunol.* 107, 842–853 (1971)] found that partial purification of bovine erythrocytes with 75% ethanol yielded a crude glycoprotein extract which showed greater reactivity with heterophile antibodies than similarly obtained crude glycoprotein extracts from horse, sheep or goat erythrocytes. This reactivity conclusion was based on results of each of three test methods which measured hemagglutination inhibition, quantitative precipitation and agar gel diffusion.

Apart from the foregoing and related work of the present inventor and coworkers, those diagnostic tests for IM which have been reported that are based on bovine erythrocyte antigens employ crude, insoluble extracts as the purest form of the reactive principle in bovine erythrocytes. For example, see U.S. Pat. Nos. 3,826,821; 3,840,655; 3,959,456; and 4,228,148.

The present invention involves the further purification of bovine erythrocytes to an essentially homogeneous glycoprotein, the homogeneity of which is shown by polyacrylamide gel electrophoresis in the presence of the protein denaturant sodium dodecyl sulfate. By utilizing a somewhat purified form of this BGP for IM detection, at least a 10-fold increase in sensitivity in the hemagglutination inhibition test is obtained, relative to the result obtained with the crude extract of bovine erythrocytes described in the 1971 Fletcher, et al. paper. This somewhat purified form contains complex glycolipid material. The results obtained with this form were reported publicly on March 27, 1980 by the present inventor and coworkers in *J. Clin. Microbio,* 11, 256–262 (1980). By removal of the glycolipid to obtain the preferred homogeneous BGP of this invention, it has been possible to develop a practical and highly useful radioimmunoassay for the detection and monitoring of human infectious mononucleosis.

As might be expected from their greater senstivity, bovine erythrocyte antigens have been shown by Evans [*J. Infect. Dis.* 132, 546–554 (1976)] to exhibit the lowest incidence of false positives as compared to erythrocytes of other species e.g. sheep and horse.

Purification of bovine erythrocyte antigen in accordance with the invention has enabled detailed characterization of the antigen itself, including determination, e.g., of the structure of the antigenic site, and establishment of how the said site is similar to one or more antigens of Epstein-Barr virus, the etiological agent of human infectious mononucleosis.

The present invention embraces the use of both partially purified BGP containing complex glycolipid and homogeneous BGP in the diagnosis and monitoring of infectious mononucleosis by means of a latex bead test. Thus, purified BGP, when covalently coupled to latex beads or particles, can be used to detect or quantify IM antibody in a glass slide test wherein hemagglutination inhibition is measured. This test takes in the order of about five minutes to perform, does not require any time-consuming pretreatment of serum before agglutination and does not require that erythrocytes in the test sample be preserved intact. This latex text affords accuracy at least as good as that obtained with a stabilized horse erythrocyte spot test in current conventional use, having given 90% agreement when tested with some 99 serum samples. For a description of this spot test, see Lee et al., *Amer. J. Clin. Pathol.* 49, 12–18 (1968).

The preferred homogeneous BGP of this invention and the opportunity it affords for development of sensitive immunoassays may make possible a rapid and useful means of detecting and quantifying antibody to Epstein-Barr virus per se, as distinguished from the heterophile antibodies that are detected by test methods of the prior art. The need for such a practical test has been recognized, e.g., in a recent editorial in *Brit. Med. J.* 280, 1153–1154 (1980).

BRIEF DESCRIPTION OF THE INVENTION

The present invention affords a novel purification procedure for obtaining two forms of antigenic bovine glycoprotein (BGP) from bovine erythrocytes, each of which acts as an antigen in testing for the presence of heterophile antibodies of human infectious mononucleosis.

In its partially purified form the BGP contains up to about 10% by weight of a complex glycolipid. It forms a single band upon gel electrophoresis at pH 7.0 when stained with either Coomassie blue or a Schiff reagent containing periodic acid, on a phosphate-buffered 7.5% polyacrylamide gel in a dilute detergent such as sodium dodecyl sulfate.

In its preferred most purified, or homogeneous, form, the BGP of this invention contains essentially no complex glycolipid. The homogeneous BGP of this invention forms substantially a single band upon gel electrophoresis at pH 7.0 when stained with either Coomassie blue or a Schiff reagent containing periodic acid, on a phosphate-buffered polyacrylamide gel in a dilute detergent such as sodium dodecyl sulfate.

The amino acid composition of the partially purified and homogeneous BGP, in moles per 100 moles of BGP is aspartic acid about 7.2, threonine about 8.0, serine about 7.2, glutamic acid about 16.5, proline about 12.9, glycine about 8.9, alanine about 5.6, valine about 5.4, methionine about 1.2, isoleucine about 6.4, leucine about 9.2, tyrosine about 0.9, phenylalanine about 2.8, histidine about 1.3, lysine about 1.8 and arginine about 4.8. Minor variations principally attributable to differences among individual cows used as sample sources will, of course, be observed as those of ordinary skill in the art will readily understand. The invention also affords two methods for diagnosing and/or monitoring the course of human infectious mononucleosis. The first is a glass slide test which measures hemagglutination inhibition of a human test sample by either of the purified forms of BGP of this invention, covalently coupled or absorbed to a latex bead. The second method is an immunoassay method, preferably a radio-immunoassay method, which utilizes the homogeneous BGP of this invention as antigen against IM heterophile antibodies contained in a human body fluid sample.

DETAILED DESCRIPTION OF THE INVENTION

The purification procedure of this invention involves a complex series of steps. In sequence, hemoglobin protein is first removed from red cell membranes, which are then extracted by a sequential organic solvent treatment which yields a crude BGP comprising a 75% ethanol extract. These preliminary steps were first described by the applicant and a coworker in 1971; see Fletcher et al. cited supra.

According to the present invention the extract obtained with 75% ethanol is further treated chromatographically on a cation-exchange column and then extracted with a series of at least two different lipid solvents to yield a product which contains up to about 10% by weight of complex glycolipid admixed with BGP. This product exhibits a single band at pH 7.0 in a gel electrophoresis test wherein the product is stained with Coomassie blue or a Schiff reagent containing periodic acid, and the gel is phosphate-buffered polyacrylamide gel in a dilute detergent solution, e.g. 0.1% sodium dodecyl sulfate.

In a final series of steps performed according to this invention, the complex glycolipid is substantially entirely removed by binding the product on an anion exchange column and eluting with a high salt buffer. This product exhibits substantially a single band at pH 7.0 in a gel electrophoresis test wherein the product is stained with Coomassie blue or a Schiff reagent containing periodic acid, and the gel is phosphate-buffered polyacrylamide gel in a dilute detergent solution, e.g. 0.1% sodium dodecyl sulfate.

It has been found that the homogeneous BGP contains essentially no glycolipid. Homogeneous BGP contains approximately 75% protein and 25% carbohydrate.

It has also been found that the glycolipid removed by this series of steps is essentially nonreactive to antibodies which characterize human infectious mononucleosis. Its removal is of special importance to the achievement of a practical immunoassay method, however, because in these methods, one must be able to assume that the label (whether a radioactive isotope, a fluorogen, a chromogen, a luminescent material or another known type of label) is substantially entirely bound to a specific immunochemical reactant. Inadvertent labelling, even of a material inert to all other substances present, renders this assumption invalid and leads to results that are invalid or unable to be reliably interpreted. Moreover, a labelled contaminant, even if nonreactive with the immunochemical entity being assayed for, may well be reactive with another component in a test sample and hence may contribute to the magnitude of readings obtained, thereby disrupting the assay and causing it to give false information. It is therefore essential to the development of successful immunoassays for diagnosis and monitoring of human IM that the complex glycolipid be essentially completely removed from BGP to be used in such immunoassays.

The partially purified BGP of this invention not only exhibits a single band in an electrophoresis test on phosphate-buffered SDS - modified polyacrylamide gel at pH 7.0, but its composition is markedly different from that of the crude bovine antigen preparation described by applicant and coworker in 1971. The following table compares the molar ratios of constituent sugars present in the crude and partially purified products:

TABLE I

| Sugar | Crude BGP Antigen | Partially Purified BGP (containing about 10% glycolipid) |
|---|---|---|
| Hexose | 2 | 1.4 |
| Sialic Acid | 1 | 1 |
| N—acetylgalactosamine | 0.7 | 0.4 |
| N—acetylglucosamine | 1 | 0.5 |

Table II shows the carbohydrate composition of the partially purified BGP of this invention, still containing about 10% of complex glycolipid, in micro-moles per milligram of protein:

TABLE II

| Sugar | Micro-mol/mg of protein |
|---|---|
| Galactose | 0.526 |
| Mannose | 0.033 |
| N—acetylglucosamine | 0.191 |
| N—acetylgalactosamine | 0.172 |
| Sialic Acid | 0.389 |

The values in Table II, except for that of sialic acid, were obtained by a conventional gas - liquid chromatography technique after first hydrolyzing the sugar at 100° C. for 3 hours in 3N HCl. The value for sialic acid was determined conventionally by the alkaline - Ehrlich test and was calculated as N-glycolylneuraminic acid. Table II was reported in Levey, B. A. et al., *J. Clin. Microbio.* 11, 256 (1981).

Table IIa shows the carbohydrate composition of the homogeneous BGP of this invention, as obtained on a different sample taken from a different bovine individual from that on which the Table I and II figures were obtained.

TABLE IIa

| | micro moles/mg glycoprotein | g/100 g glycoprotein |
|---|---|---|
| Polypeptide | 7.163 | 73.30 |
| N—glycolylneuraminic acid | .297 | 9.17 |
| Galactose | .448 | 7.26 |
| N—acetylglucosamine | .322 | 6.54 |
| N—acetylgalactosamine | .161 | 3.27 |
| Mannose | .028 | 0.46 |

The values in Table IIa, except for N-glycolylneuraminic acid and polypeptide content, were obtained by a conventional gas-liquid chromatography technique after first hydrolyzing the sugar at 100° C. for about 3 hours in 3 N HCl. The value for N-glycolyneuraminic acid was determined conventionally by the alkaline - Ehrlich test.

The homogeneous bovine glycoprotein has approximately 75 weight % of protein and 25 weight % carbohydrate. Minor variations in determinations such as these were found. One variation was between the sample used for Tables I and II, and the sample used for Tables IIa and IIb. Specifically the sample used for Tables I and II had a weight % of protein equal to approximately 77% and a weight % of carbohydrate equal to approximately 23%, whereas the sample used for Tables IIa and IIb had a weight % of protein equal to approximately 73% and a weight % of carbohydrate equal to approximately 27%. As those skilled in the biological arts will readily understand, such differences between individual and individual are minor and are to be expected from samples of individual origin.

Since the weight % of protein was approximated from the number moles of amino acids subjected to amino acid analysis, the observed differences in weight % are also attributable, of course, to different amino acid analyzers used for each sample, and to different buffer systems employed in the amino acid analyzer.

Table IIb compares the molar ratios of constituent sugars present in the partially purified BGP and in the homogeneous BGP.

TABLE IIb

| Sugar | Partially Purified BGP (containing 10% glycolipid) | Homogeneous BGP (with glycolipid removed) |
|---|---|---|
| N—glycolylneuraminic acid | 1 | 1 |
| Galactose | 1.35 | 1.50 |
| N—acetylglucosamine | 0.49 | 1.08 |
| N—acetylgalactosamine | 0.44 | 0.54 |
| Mannose | 0.08 | 0.09 |

Note that the homogeneous BGP of this invention has a substantially higher molar ratio of N-acetylglucosamine to N-glycolylneuraminic acid, indicating that removal of the complex glycolipid from the partially purified BGP significantly changed the carbohydrate composition. It should also be borne in mind that this comparison was made using two different samples obtained from different bovine individuals, and that individual differences among living things to some extent always affect numerical values obtained.

Table III compares the partially purified BGP of this invention with the crude BGP reported by applicant and coworker in 1971, in terms of amino acid composition in moles per 100 moles of total BGP present. These values were determined by hydrolyzing samples in 6 N HCl at 110° C. in sealed, evacuated tubes for a 24 hour period, chromatographing the product so obtained and analyzing with a Durran 500 automatic amino acid analyzer. No corrections were made for loss due to hydrolysis.

TABLE III

| Amino Acid | Crude BGP Antigen | Partially Purified BGP |
|---|---|---|
| | Moles/100 moles | |
| Aspartic acid | 7.8 | 7.2 |
| Threonine | 8.3 | 8.0 |
| Serine | 10.0 | 7.2 |
| Glutamic acid | 16.9 | 16.5 |
| Proline | 12.4 | 12.9 |
| Glycine | 7.8 | 8.9 |
| Alanine | 4.3 | 5.6 |
| Valine | 5.3 | 5.4 |
| Methionine | 0.3 | 1.2 |
| Isoleucine | 5.2 | 6.4 |
| Leucine | 9.5 | 9.2 |
| Tyrosine | 0.8 | 0.9 |
| Phenylalanine | 3.0 | 2.8 |
| Histidine | 0.5 | 1.3 |
| Lysine | 2.9 | 1.8 |
| Arginine | 5.3 | 4.8 |
| Total | 100.3 | Total 99.9 |

It will be understood that the homogeneous BGP of this invention has essentially the same amino acid composition as the partially purified BGP of the invention, allowing for individual variations in samples from different animals. The two forms differ principally in the substantially complete removal of complex glycolipid from the latter to produce the former.

Thus the homogeneous BGP as determined on a sample from a different bovine individual from that donating the Table III sample, has been found to have the following amino acid composition.

TABLE IIIa

| Amino Acid | moles/100 moles |
| --- | --- |
| ½ cystine | 0.5 |
| Aspartic acid | 6.2 |
| Threonine | 8.8 |
| Serine | 7.5 |
| Glutamic acid | 16.4 |
| Proline | 13.9 |
| Glycine | 9.9 |
| Alanine | 5.0 |
| Valine | 5.0 |
| Methionine | 1.8 |
| Isoleucine | 5.3 |
| Leucine | 7.7 |
| Tyrosine | 0.5 |
| Phenylalanine | 3.0 |
| Histidine | 1.1 |
| Lysine | 2.6 |
| Arginine | 4.8 |
| tryptophane | 0.2 |
| Total | 100.0 |

The values in Table IIIa were determined by hydrolyzing homogeneous BGP in 6 N HCl at 110° C. for 24 hours and ascertaining test values for each amino acid with a JOEL 5EOL 5AH amino acid analyzer. ½ cys data is from analysis of BGP alkylated with iodoacetate prior to hydrolysis and methionine and tryptophane values are from sample hydrolysed in 4 N methane sulfonic acid at 100° C. for 20 hr in vacuo. Threonine and serine were corrected respectively, for 5% and 10% losses due to hydrolysis. The observed differences in amino acid composition between partially purified BGP (Table III) and homogeneous BGP (Table IIIa) are insubstantial and are attributed, inter alia, to the dependence of extent of HCl hydrolysis on the presence of contaminating macroglycolipids, to different amino acid analyzers use to analyze each form of BGP, and to well-recognized individual differences among cows used to prepare each form of BGP. It will be understood that the amino acid composition of the partially purified BGP is substantially the same as that of the homogeneous BGP.

The purification procedures by which the partially purified BGP and homogeneous BGP of this invention are obtained comprise three essential stages, as follows:

A. Preparation of a crude BGP antigen from bovine red blood cells

Hemoglobin-free stroma is isolated by extraction of stroma, i.e. membranes, as generally described in Fletcher et al., *J. Imm.* 107, 842 (1971). More particularly, to fresh blood from newly slaughtered cattle, an anticoagulant is added to prevent clotting. Almost any conventional anticoagulant may be used, except that heparin and ethylenediamine tetraacetic acid must be avoided. Preferred anticoagulants include acidified citrate-dextrose, oxalate and Alsievers. The blood may be stored at normal refrigeration temperatures for up to about 24 hours. Is is then thoroughly washed with any of the common isotonic buffers at a pH that preserves the integrity of the cell membrane, i.e., in the order of about 5.0 to about 9.0, preferably about 6.0 to about 8.0 such as phosphate-buffered saline of pH about 7.4, or Tris-buffered saline of pH about 7.4. If the blood samples are allowed to stand for a period appreciably longer than about 24 hours prior to washing, the samples may become contaminated with bacteria or with lysosomal enzymes from white blood cells. For each washing step, the cells are suspended in buffer and then centrifuged. After centrifugation, the supernatant and buffy coat are removed by aspiration. These washing-centrifugation-aspiration steps are continued until the buffy coat is substantially completely removed and the supernatant is essentially clear and free from color. It is important to remove substantially all of the buffy coat because it is a source of hydrolytic enzymes. Approximately one quarter of the total volume of erythrocytes is typically lost during the washing steps.

Washed and packed erythrocytes are then lysed in hypotonic buffer of alkaline pH, i.e. above at about 8.0. The lysing buffer must be alkaline to prevent denaturation of hemoglobin and unwanted binding of denatured hemoglobin to membranes. Cell stroma or membranes are packed together by centrifugation at about 13,000 xg for 1 hour at a temperature in the order of about 4° to about 15° C. The supernatant is aspirated and discarded, where upon the loosely packed membrane layer is decanted from the red pellet. This procedure of alkaline washing followed by cold centrifugation and separation steps is repeated until the decanted membrane layer is creamy white, i.e., without visible hemoglobin contamination. The purified stroma must then be dried, e.g., by freeze-drying to carry out the next steps.

Thereafter, an even suspension is acetone of freeze-dried, hemoglobin-free stroma from bovine erythrocytes is prepared by grinding in mortar and pestle about 1 gram of stroma with, preferably, about 200 ml acetone. The acetone must be anhydrous, and taken from a freshly opened bottle. The volume of acetone per gram of stroma may vary from as low as about 100 ml up to a volume substantially greater than 200 ml. The suspension is refluxed, normally for about 3 hours, but the time may vary from about 1 to 6 hours. The residue is collected by filtering of the acetone while the suspension is still warm; otherwise there is some unwanted precipitation of acetone-soluble neutral lipids on the filter. The residue is thoroughly washed with acetone preferably warm acetone, and air dried.

The same refluxing procedure is repeated on the acetone extracted residue, this time substituting anhydrous, 100% ethanol for the acetone. Extraction with 100% ethanol removes some but not all of the glycolipids. The ethanol extract is discarded, and the residue is dried. The acetone and ethanol extract residue is refluxed again, preferably with about 75% aqueous ethanol but a solution of between about 50% and about 80% aqueous ethanol may be used. The supernatant is removed by filtration and set aside. The residue is then washed with an equal volume of the aqueous ethanol. The washed residue is discarded. The extract and all the washings are combined, concentrated, dialyzed to remove salt and freeze-dried in a conventional manner. Alternatively the aqueous ethanol extract and its washings may be combined, concentrated, dialyzed against water and stored under normal refrigeration temperatures.

B. Isolation of Partially Purified BGP of This Invention

The lyophilized aqueous ethanol extract from Step A is redissolved in water and precipitated with about 90% aqueous ethanol. Incubation on ice for at least 2 hours and addition of a salt, e.g., 3 or 4 crystals of sodium acetate or other common salt, can help to initiate precipitation. Typically, a massive, white precipitate appears. This precipitate is centrifuged and the supernatant is removed and discarded. The precipitate is then dialyzed against a conventional buffer of low ionic strength and low pH in preparation for passage through a cationic exchange column.

Chromatography on a cationic exchange resin is best performed at a pH of from about 4 to about 6, e.g., above the isoelectric focusing point of the bovine glycoprotein reactive with heterophile antibodies. Resins appropriate for this step include phosphocellulose, carboxymethyl cellulose, and any of the weakly acidic acrylic resins commonly employed for purification of proteins. After the resin is preequilibrated with the low ionic strength, low pH buffer, the dialyzed protein sample is passed through the column. Neutral and basic contaminants are bound by the column and discarded. Those fractions which contain sialic acid and do not bind the column are collected. They can be dialyzed against water and freeze-dried or lyophilized if desired.

The collected fractions, preferably but not necessarily in lyophilized form are next treated. If lyophilized or otherwise dried, the fractions are first dissolved in water, about 5 volumes of diethyl ether: ethanol (in a volume to volume ratio ranging from about 4:1 to about 1:1) are next added and the mixture is centrifuged and permitted to settle. Two phases appear, one aqueous and one comprising diethyl ether. The aqueous layer is removed and freeze-dried to remove residual ether and water.

Another extraction with a different lipid solvent from eithyl ether is then performed, in accordance with conventional techniques of chemistry. In this procedure, the lyophilized extract from the first extraction step is dissolved in water and reextracted in about 9 volumes of chloroform/methanol in the ratio of about 2:1, volume by volume. The mixture is again centrifuged and permitted to separate into an aqueous phase and an organic phase. The separated aqueous phase is removed and lyophilized. The lyophilized material is the partially purified BGP of this invention.

C. Preparation of Homogeneous BGP of This Invention.

In order to remove contaminants still remaining principally comprising complex glycolipids, the partially purified, lyophilized BGP form Step B is dissolved in a low ionic strength buffer containing about 1% neutral detergent, such as Emulphogen or Triton-X-100. This detergent aids in dissolving the complex glycolipid. The solution is loaded onto an anion exchange column, preequilibrated with low ionic strength buffer. A variety of suitable anion exchange resins are commercially available, including DE-52 cellulose, DEAE B10-GEL A and Cellex D. The column is washed with the low ionic strength aqueous buffer until the optical density of the fractions eluted has returned to the level of a blank solution consisting of the buffer alone, normally less than 0.1 units at 280 nanometers. The column is then eluted with aqueous buffer containing high salt concentration, i.e. in the order of more than 0.3 molar concentration of a common salt such as NaCl, Na acetate, KCl, etc. High concentrations of salt compete with the electrostatic interactions between the BGP and the cationic resin, so as to pool a single peak of material. The material is dialyzed against $H_2O$, freezedried and held for use.

USE OF THE PARTIALLY PURIFIED AND HOMOGENEOUS BGP OF THIS INVENTION

Tests have shown that more than ten times as much crude BGP antigen (Step A above) is needed to completely inhibit the agglutination of sheep erythrocytes by IM antiserum as is needed of the partially purified BGP from Step B above. Table IV shows the results:

| Preparation | Amount in micrograms per milliliter needed for Complete Inhibition |
|---|---|
| 1. Product of Step A | 1.0 |
| 2. Product of Step B | 0.08 |

When the product of Step C, the homogeneous BGP, is substituted for the product of Step B, the amount necessary for inhibition is somewhat lower still.

Either of the products of this invention is useable in the latex bead test for diagnosing and/or monitoring human infectious mononucleosis.

1. Latex Bead Test

Chemical coupling of either purified BGP of this invention to a carrier particle can be accomplished in a variety of ways. Particles composed of a synthetic polymer such as polystyrene, poly (methyl methacrylate) or any synthetic latex are preferred over microbial cells due to their enhanced stability during long term storage. In general, the beads or particles should have free functional groups such as one or more of the primary amino, sulfhydryl, carboxyl or hydroxyl groups. Various methods of coupling proteins to carrier particles composed of a synthetic polymer are discussed in the literature, including inter alia in U.S. Pat. Nos. 4,046,723; 3,882,224; 3,857,931; 3,639,558. In the preferred method of coupling latex beads to a BGP of this invention, the BGP is added to a suspension of about 0.25% (in water) of carboxyl-modified, uniform latex particles. The mixture is stirred for at least about 30 minutes. The pH is maintained between about 4 to and about 6. Then a substituted carbodiimide such as, e.g., 1-ethyl-3-(3-dimethyl amino propyl) carbodiimide-hydrochloride, is added, in a freshly made solution with a minimum amount of water. This carbodiimide is added in an amount to provide a final concentration thereof in the order of about 0.1M. A pH below 7 is maintained for at least one hour, and the mixture is then stirred overnight or longer. The particles are washed alternatively in an aqueous buffer of low pH (about 4.0) then in an aqueous buffer of higher pH (about 8), and finally washed twice with distilled water. The beads containing coupled BGP of this invention are then stored in the higher aqueous pH buffer (about 8) at concentrations of about 1%.

To conduct a test of infectious mononucleosis, BGP-latex beads are diluted in buffer to a concentration in the order of about 0.25% (w/v). Appreciably lower concentrations of the reagent prevent agglutination that is easily visible, while appreciably higher concentrations result in waste of protein bound carrier particles. Serial dilutions in buffer are made of the test antiserum or biological fluid such as serum. One drop of each such dilution is added to one drop of BGP-latex bead reagent within the ceramic ring of a well in a serological ring slide. The slide is rotated briefly to mix antiserum or serum and latex reagent, and agglutination is determined by visual inspection. The end points of the titration are determined as the highest dilution (i.e., most dilute concentration) of serum giving visible clumping. Other containers may be used for the agglutination test, such as the polystyrene microtiter plates with U-shaped wells from Cooke Engineering Co., but agglutination is more difficult to read in such wells.

2. Immunoassay Using Homogeneous BGP of This Invention

Many types of immunoassays, including radioimmunoassays, are known in the art and can be employed for the detection and/or quantitation of homogeneous BGP of this invention. An immunoassay may use, for example, a radioactive tag for the antigen, such as $^{125}I$, $^{131}I$, $^{3}H$ or $^{14}C$, or any other radioisotope easily and conveniently measured. Other methods of tagging the antigen include attachment of a fluorogen, chromophore, enzyme or luminescent tag. Numerous methods of separating antibody-antigen complexes from free, (i.e. unbound) antigen are known, including precipitation of antibody (double antibody). Among other known techniques are those using solid support matrices, also known as a solid-phase assay wherein glass, silica or plastic beads or unitary plastic inserts are used to fix one component of the antigen-antibody pair.

A preferred way to tag homogeneous BGP of this invention is with $^{125}I$, a radioactive label that can yield labelled antigens with very high specific activity, as measured in terms of the rate of detectable disintegrations per microgram of protein.

BGP is labeled with $^{125}I$ to a specific activity of about 1 micro Curie/microgram of protein by one of a variety of methods known in the art such as e.g., lactoperoxidose, chloramine-T labeling, or Iodogen [Fraker, P. J. & J. C. Speck, *Biochem. Biophys. Res. Commun.* 80. 849 (1978)]. The labeled protein is separated from unreacted free $^{125}I$ by gel filtration with e.g., Sephadex G-50, Sephadex G-25, Sephadex G-10, or any of the porous polyacrylamide beads exhibiting molecular weight exclusion limits less than about 100,000.

A preferred immunoassay based on $^{125}I$-labeled homogeneous BGP, is the competitive radioimmunoassay. The principle of the competition radioimmunoassay is that labeled antigens compete with unlabeled antigens for the same combining sites of the antibody in the serum. See, e.g., Kabat, E. (1976) Structural Concepts in Immunology and Immunochemistry Holt, Richard and Winston. Separation of antibody-antigen complexes from free antigen allows the determination of the amount of antigen bound. This well-known assay has many variations, for example, testing a variety of unlabeled antigens to determine which unlabeled antigen has the greatest similarity to the labeled antigen. Another variation, used for the BGP, is to test a standardized quantity of radio-labeled and unlabeled antigen against samples from each of many dilutions of a variety of test antisera with the purpose of obtaining a quantitative measure of the titer of specific antibody in any antiserum. This is done by determining the relative amount of radioactive antigen bound by the test antiserum and comparing this quantity with the amount bound by a control antiserum of the same dilution as the test antiserum.

It should be noted that variations within the scope of this invention also include competitive radioimmunoassays using non-radioactive tags for BGP such as a fluorogen, chromophore, luminescent material or enzyme.

There are many methods known in the art for separating antibody-antigen complexes from free antigen. One method usable with e.g. homogeneous BGP of this invention is the solid-phase, sandwich-type immunoassay. In this method, microtiter plates, preferably made of a material easily cuttable by scissors and with round bottom wells, are coated by incubation in each well of about two micrograms homogenous BGP with about 200 microliters of aqueous buffered saline solution overnight. Most suitably, this step is effected in a moist chamber to prevent drying.

The wells are then emptied by aspiration, washed at least once with aqueous buffered saline and filled with a solution of protein carrier in aqueous buffered saline. The protein carrier blocks any binding sites on the inside of the well, or the solid-phase, that were not bound by purified BGP added in the first step. Typical solutions of protein carrier used for coating wells are e.g., gelatin, goat serum albumin, rabbit serum albumin, or egg ovalbumin in the concentration ranges of from about 0.05% to about 0.2%. In this assay, *bovine* serum albumin should not be used as a protein carrier because it might interfere with specific binding to homogeneous *bovine* glycoprotein. The plates are incubated with carrier solution for at least 1 hour with gentle agitation or mixing to enhance uniform coating of the well.

The wells are then emptied again by aspiration, washed two to five times with aqueous buffered saline, preferably three times, and then about 200 microliters of suitably diluted serum sample is added to each well. This step binds the antigen to specific antibody. The plates are incubated to equilibrate the antibody with the antigen, for instance at room temperature overnight, preferably in a moist chamber to prevent drying.

The wells are emptied a third time by aspiration, washed about 5 times, then about 10,000 cpm (counts per minute) of $^{125}I$-homogeneous BGP suitably diluted in carrier protein (e.g., 0.1% egg ovalbumin in aqueous buffered saline) is added to each well in a total volume of about 200 microliters. Radiolabeled protein is allowed to equilibrate with binding sites on the antibody still available to the antigen, with, for example, an incubation overnight.

The contents of each well are aspirated for the fourth time, and each well washed at least three times with aqueous buffered saline. The plates are air dried about 6 hours, then their wells are cut out with scissors, and radioactivity is counted in a conventional counter. For $^{125}I$, one minute counts are normally sufficient for reasonable accuracy.

EXEMPLARY PROCEDURES

EXAMPLE 1

Preparation of Hemoglobin-Free Stroma From Blood

Fresh blood was obtained at the time of slaughter in anti-coagulant citrate - dextrose solution. The blood was allowed to stand at 4° C. for about 24 hours, then centrifuged at about 2,500 rpm for about 30 minutes at 4° C. to pellet erythrocytes. The supernatant (plasma) and intermediate cell layer (buffy coat) were removed.

The erythrocytes were then washed three times in an equal volume of cold 0.12M NaCl 0.05M sodium phosphate buffer, about pH 7.4. For each washing step, the cells were suspended in buffer, then centrifuged at about 2,500 RPM for 20 minutes. After centrifugation, the supernatant and remaining buffy coat were aspirated. Approximately one quarter of the total volume of erythrocytes was lost in removing the buffy coat, which contains undesired lymphocytes.

Washed and packed erythrocytes were lysed in nine volumes of cold 0.005M aqueous sodium phosphate, pH about 8.0. Membranes were then pelleted by centrifugation at about 13000-xg for 60 minutes at 4° C. The supernatant was aspirated and discarded whereupon the loosely packed membrane layer was decanted from the red pellet. This procedure of washing the membranes was repeated until the decanted membrane layer was creamy white. Hemoglobin-free stroma were freeze-dried for storage.

EXAMPLE

Isolation of Partially Purified Bovine Glycoprotein of This Invention

Hemoglobin-free stroma were isolated as described in Example 1, then subjected to extractions in acetone, 100% ethanol and 75% aqueous ethanol as described in the specification hereinabove. The 75% ethanol extract in lyophilized form was redissolved in one volume of $H_2O$, and 9 volumes of absolute ethanol was added plus 3 or 4 crystals of sodium acetate. The mixture was stirred at 4° C. for two hours, then centrifuged at 1000 xg to separate the 90% aqueous ethanol precipitate from the supernatant, which was discarded. The precipitate was dialyzed against 0.02M sodium citrate buffer, pH 4.1, and applied to a phosphocellulose column (8×2.5 cm) pre-equilibrated with 0.02M citrate buffer, pH 4.1. Neutral and basic contaminants which were bound by the column were discarded. Fractions containing sialic acid (about 100 ml) were collected, dialyzed against $H_2O$ and lyophilized. Sialic acid can be estimated by the resorcinol method [Stennerholm, L. *Biochem. Biophys. Acta* 24, 604 (1957)] using N-acetyl neuraminic acid and N-glycolyl neuraminic acid as standards.

The chromatographed sialoglycoprotein was then extracted twice the lipid solvent and alcohol mixtures to remove lipid contaminants as follows. The lyophilized glycoprotein was dissolved in $H_2O$, then 5 volumes of diethyl eter; ethanol (4:1, volume by volume) were added, and mixed for 30 minutes, and the aqueous phase removed, and freeze-dried. The dried material was then reextracted by dissolving in $H_2O$ and adding 9 volumes of chloroform:methanol (2:1, volume by volume). The mixture was stirred for 20 minutes at room temperature and centrifuged at 2000 RPM for 30 minutes. The aqueous phase was removed and lyophilized to yield the partially purified BGP of this invention. Polyacrylamide gel electrophoresis of this material (50 micrograms) in 0.1% sodium dodecyl sulfate, 0.0M phosphate buffer (pH 7.0) gave a single band in the gel after staining with either Coomassie blue or periodic acid-Schiff reagent.

EXAMPLE 3

Freeze-dried product from Example 2 was dissolved in 0.05M Tris buffer of pH 8.0 containing 1% emulphogen (GAF Corporation), and loaded onto a DE-52 cellulose column (18×1 cm) equilibrated with 0.05M Tris Buffer pH 8.0. The column was washed with the same buffer until the optical density at 280 nm returned to background level. The bound BGP was eluted with 0.05M Tris pH 8.0, containing 0.5M NaCl. Fractions of the single peak of optically absorbing material (280 nm) were pooled, dialyzed against $H_2O$ and freeze-dried.

EXAMPLE 4

Preparaton of BGP-latex beads

Partially purified BGP made as in Example 2 from bovine erythrocytes (31 micrograms/ml) was added to a 0.25% suspension in water of carboxyl-modified, uniform latex particles, 0.455 microns average diameter (Source: Dow Diagnostics). The mixture was stirred for 30 minutes at room temperature, and the pH maintained at 4–6. Then 1-ethyl-3-(3-dimethylaminopropyl) carbodiimide-hydrochloride, freshly dissolved in a minimum amount of water, was added to a final concentration of 0.1M. The pH was maintained at about 5.5 for 1 hour, and the mixture was stirred at room temperature for 18 hours. The particles were then washed alternatively in a buffer containing 0.1M glycine, 0.15M NaCl, 7 mM $CaCl_2$ (GBS) at pH 4.0 and then at pH 8.0, and finally they were washed twice with distilled $H_2O$. Between each wash, the particles were centrifuged at 17,000 xg for 20 minutes. For storage, the glycoprotein-latex beads were diluted to a concentration of 1% in GBS at pH 8.3 and kept at 4° C. Before use the reagent was diluted to 0.25% with the same buffer.

EXAMPLE 5

Latex slide test with latex beads coupled to partially purified BGP

Aliquots of 25 microliters of a 0.25% suspension (in GBS) of the latex beads of Example 4 were added to each well within ceramic rings on a serological ring slide (about 7.9×12.1 cm; Source: Scientific Products). Serial two-fold dilutions (in GBS) of test antisera were made in test tubes (10×65 mm) and 25 microliter samples were added to each aliquot of the latex bead suspension. The slide was rotated on a Thomas Clinical Rotator at 1,500 r/p.m. for about 5 minutes at room temperature, and read immediately. Agglutination was determined by macroscopic examination. The end points of the titration were recognized as the highest dilution of antiserum giving visible clumping as compared to a latex suspension incubated with a serum known to lack detectable heterphile antibodies.

EXAMPLE 6

The procedure of Examples 4 and 5 is repeated, substituting homogeneous BGP of Example 3 for the partially purified BGP of Example 2.

EXAMPLE 7

Radioimmunoassay based on $^{125}I$ -homogeneous BGP of Example 3

The wells of polystyrene microtitre plates (U-bottom; Source: Cooke Engineering Co.) were each coated with 2 micrograms of homogeneous bovine glycoprotein from Example 3 in 200 microliters phosphate-buffered saline (PBS) overnight at room temperature in a moist chamber. The wells were emptied by aspiration, washed three times with PBS and filled with 0.1% gelatin in PBS. The plates were then incubated at room temperature for 1 hour on a Cortis Laboratories micromixer. The wells were then emptied by aspiration, washed three times in PBS and 200 microliters of suitably diluted serum was added. The plates were incubated overnight at room temperature in a moist chamber, then emptied and washed five times with PBS. About 10,000 cpm $^{125}$I-BGP, specific activity about 1 microcurie/microgram purified bovine glycoprotein, in 0.05% bovine serum albumin was added to each well in a volume of 200 microliters. The plates were incubated overnight, the contents of each well were aspirated, and each well was washed three times with PBS. The plates were air dried. Before counting, each well was cut out with scissors and the radioactivity counted (one minute counts per sample) in a counter.

ples 4 and 5 and the fresh horse erythrocyte differential test of the prior art. Another test also employed was the competitive radioimmunoassay based on $^{125}$I-purified horse glycoprotein as described by the inventor and coworkers, [see Fletcher, et al., *J. Immunol. Meth.* 14, 51–58 (1977)], an assay using $^{125}$I-horse GP with a specific activity of about 2 microcuries/microgram of glycoprotein. The results are shown in Table V. This table demonstrates that the competitive radioimmunoassay based on $^{125}$I-homogeneous BGP is more sensitive than the one based on $^{125}$I-purified horse GP. The conventional spot test gave false positives, e.g., patients 110, 128, 148.

TABLE IV

| | Radioimmunoassays | | Fresh Horse | | |
| | Horse GP | Bovine GP | Erythrocyte | Latex | Mono |
| | % cpm specifically bound | | Differential Test | Test | Test |
| --- | --- | --- | --- | --- | --- |
| Sera from patients with positive Mono Test | | | | | |
| #5 | 6.4 | 8.9 | + | + | + |
| #24 | 4.0 | 11.4 | + | + | + |
| #33 | 24.1 | 28.7 | + | + | + |
| #34 | 22.8 | 29.9 | + | + | + |
| #45 | 10.8 | 15.5 | + | + | + |
| #48 | 12.6 | 16.7 | + | + | + |
| #54 | 35.8 | 27.1 | + | + | + |
| #71 | 5.5 | 13.1 | + | + | + |
| #79 | 18.5 | 28.9 | + | + | + |
| #92 | 1.5 | 8.7 | + | + | + |
| #103 | 31.2 | 26.4 | + | + | + |
| #110 | 1.0 | 0.7 | − | − | + |
| #114 | 5.2 | 16.4 | + | + | + |
| #128 | 0.6 | 0.5 | − | − | + |
| #134 | 1.2 | 4.3 | + | + | + |
| #148 | 1.0 | 0.2 | − | − | + |
| #150 | 16.8 | 24.4 | + | + | + |
| #153 | 12.9 | 27.3 | + | + | + |
| pos. control pool | 14.2 | 21.3 | + | + | ND |
| pos. control pool | 28.5 | 28.8 | + | + | ND |
| Sera from individuals with negative Mono Test | | | | | |
| p #1 | 0.2 | 1.9 | − | − | − |
| p #2 | 0 | 0 | − | − | − |
| p #3 | 0.2 | 0.5 | − | − | − |
| p #5 | 0 | 0.1 | − | − | − |
| p #9 | 0.2 | 0.7 | − | − | − |
| p #10 | 0 | 0.1 | − | − | − |
| p #15 | 0.7 | 0 | − | − | − |
| p #16 | 0.2 | 0 | − | − | − |
| p #17 | 0.2 | 0 | − | − | − |
| p #18 | 0.2 | 0.3 | − | − | − |
| p #19 | 0.3 | 0.9 | − | − | − |
| p #20 | 0.3 | 0.1 | − | − | − |
| neg. control | 0 | 0.1 | − | − | ND |

EXAMPLE 8

Patient population survey and comparison of a variety of tests for infectious mononucleosis Patient samples were divided into two groups, those which gave a positive slide test (also known as the Monotest) for IM from patients who presented clinical signs suggestive of IM, and, secondly, samples from those individuals who had clinical signs perhaps suggestive of IM but exhibited a negative Mono Test.

The following tests were then performed; the competitive radioimmunoassay based on $^{125}$I-homogeneous BGP as described in the previous example, the BGP latex bead test using partially purified BGP as in Exam-

EXAMPLE 9

Separation of macroglycolipids from erythrocyte glycoproteins

Purification of partially purified BGP was repeated according to Example 2, except that a starting batch of bovine erythryocytes from a different cow was used. The partially purified BGP was then further purified according to the methods of Dejter-Juszynski, M. et al. Eur. J. Biochem. 83, 363 (1978), as follows. The freeze-dried product of the procedure of Example 2 was dissolved in 0.5 M Tris-HCL, pH 8.0 containing 1% Emulphogene BC-720 (GAF, New York, N.Y.) and placed on a column of DEAE-cellulose pre-equilibrated with the same buffer but without detergent. The column was eluted first with buffer then with a 0–0.5M NaCl gradient in buffer. The glycoprotein eluted as a single peak which was dialyzed and freeze-dried, yielding the homogeneous BGP of this invention. Polyacrylamide gel electrophosesis of the material (100 micrograms, an amount that overloads the gel) in 0.1% sodium dodecyl sulfate, 0.01M phosphate buffer (pH 7.0) gave a single band having an apparent MW of about 34,000 daltons, and a minor contaminant with an apparent MW of about 14,000 daltons. The minor contaminant represented less than 3% of the total amino acids, as measured by amino acid analysis with a JEOL 5EOL 5AH amino acid analyzer, after hydrolysis in 6 N HCl at 100° C. in a sealed, evacuated tube for 24 hrs.

While the invention has been described in connection with specific embodiments thereof, it will be understood that it is capable of further modifications and this application is intended to cover any variations, uses, or adaptations of the invention following, in general, the principles of the invention and including such departures from the present disclosure as are obvious to one of ordinary skill in the art to which the invention pertains and as may be applied to the essential features hereinbefore set forth, and as follows in the scope of the appended claims.

What is claimed is:

1. A bovine glycoprotein, the amino acid composition of which is in the order of about 7.2 mole % aspartic acid, about 8 mole % threonine, about 7.2 mole % serine, about 16.5 mole glutamic acid, about 12.9 mole % proline, about 8.9 mole % glycine, about 5.6 mole % alanine, about 5.4 mole % valine, about 1.2 mole % methionine, about 6.4 mole % isoleucine, about 9.2 mole % leucine, about 0.9 mole % tyrosine, about 2.8 mole % phenylalanine about 1.3 mole % histidine, about 1.8 mole % lysine and about 4.8 mole % arginine.

2. A bovine glycoprotein according to claim 1 which contains in the order of about 10% by weight of a complex glycolipid and which also contains hexose, sialic acid, N-acetylgalactosamine and N-acetylglucosamine in the approximate molar ratio 1.4:1:0.4:0.5, further characterized by its ability to give a single band upon polyacrylamide gel electrophoresis when stained with Coomassie blue or periodic acid modified Schiff reagent.

3. A bovine glycoprotein according to claim 1 which is essentially homogeneous.

4. A process for preparing the bovine glycoprotein of claim 2 which comprises the steps of:
   (a) uniformly suspending dried, ground, hemoglobin-free stroma from bovine erythrocytes in anhydrous acetone;
   (b) refluxing for from about 1 to about 6 hours, filtering and drying the residue;
   (c) suspending said dried residue in 100% anhydrous ethanol;
   (d) refluxing for from 1 to about 6 hours, filtering and drying the residue;
   (e) suspending the dried residue from step (d) in aqueous ethanol of from about 50% to about 80% strength and repeating step (b);
   (f) dissolving the residue from step (e) in water and adding 90% aqueous ethanol, followed by incubating on ice, until crystallization occurs, centrifuging and dialyzing the solid layer against a low pH, low ionic strength buffer;
   (g) passing the solid from step (f) through a cation exchange resin on a chromatographic column;
   (h) collecting the sialic acid containing fractions from the column and drying them;
   (i) treating the collected fractions from step (h) by extraction with a known lipid solvent, centrifuging, collecting the aqueous layer and drying it;
   (j) repeating step (i) on the product of that step, using a different lipid solvent, and
   (k) recovering the product of claim 2 in lyophilized form.

5. A process according to claim 4 wherein the cation exchange resin is phosphocellulose.

6. A process according to claim 4 wherein the lipid solvent of step (i) is diethyl ether and ethanol in a ratio by volume between about 4:1 and about 1:1.

7. A process according to claim 4 in which the lipid solvent of step (j) is chloroform and methanol in a volume ratio of about 2:1.

8. A process according to claim 4 wherein the solvent in step (e) is 75% aqueous ethanol.

9. A process for preparing the bovine glycoprotein of claim 3 which comprises the steps of,
   (a) dissolving the bovine glycoprotein from claim 2 in a low ionic strength buffer containing about 1% neutral detergent;
   (b) loading the solution of an anion exchange chromatographic column;
   (c) washing thoroughly with low ionic strength buffer;
   (d) eluting the column with aqueous buffer to high salt concentration, and
   (e) dialyzing the product of step (d) against water and recovering the product of claim 3 in freeze dried form.

10. A process for diagnosing infectious mononucleosis which comprises the steps of,
   (a) appending to minute particles of latex or synthetic resin the bovine glycoprotein of claim 2 or claim 3;
   (b) coating a flat surface with particles from step (a) hereof;
   (c) adding a diluted sample of biological test fluid from a patient suspected of harboring infectious mononucleosis, rotating the flat surface;
   (d) observing the degree of agglutination of the sample and,
   (e) comparing the result of step (d) with the degree of agglutination observed when a standard containing a known amount of infectious mononucleosis heterophile antibody is substituted as the sample in step (c) of the procedure recited in steps (a) through (d).

11. A bovine glycoprotein according to claim 1, containing a label selected from the group consisting of radioisotopes, fluorogens, chromophores, enzymes, luminescent substances and other known labels used in immunoassay procedures.

12. The labelled bovine glycoprotein of claim 11 in which the label is $^{125}$I.

13. A radioimmunoassay procedure for determining the quantity of heterophile antibody of human infectious mononucleosis that is present in a test fluid sample wherein the antigen for said antibody comprises labelled bovine glycoprotein of claim 12.

14. A procedure according to claim 13 in which the radioimmunoassay is of the sandwich type.

15. A procedure according to claim 13 in which the radioimmunoassay is a competition assay.

16. A radioimmunoassay procedure according to claim 15 in which bovine glycoprotein of claim 3 is bound to a solid surface.

17. A bovine glycoprotein according to claim 1 containing essentially no glycolipid and having a carbohydrate content of approximately 25 weight percent, comprising hexose, sialic acid, N-acetylgalactosamine and N-acetylglucosamine in the approximate molar ratio of 1.6:1.0:0.5:1.1, further characterized by a protein content of approximately 75 weight percent and by its ability to give essentially a single band upon polyacrylamide gel electrophoresis when stained with Coomassie blue or with periodic acid modified Schiff reagent.

18. A process for preparing the bovine glycoprotein of claim 17 which comprises the steps of,
   (a) dissolving the bovine glycoprotein from claim 2 in a low ionic strength buffer containing about 1% neutral detergent;
   (b) loading the solution on an anion exchange chromatographic column;
   (c) washing thoroughly with low ionic strength buffer;
   (d) eluting the column with aqueous buffer to high salt concentration, and
   (e) dialyzing the product of step (d) against water and recovering the product of claim 17 in freeze dried form.

19. A process for diagnosing infectious mononucleosis which comprises the steps of,
   (a) appending to minute particles of latex or synthetic resin the bovine glycoprotein of claim 17;
   (b) coating a flat surface with particles from step (a) hereof;
   (c) adding a diluted sample of biological test fluid from a patient suspected of harboring infectious mononucleosis, rotating the flat surface;
   (d) observing the degree of agglutination of the sample and,
   (e) comparing the result of step (d) with the degree of agglutination observed when a standard containing a known amount of infectious mononucleosis heterophile antibody is substituted as the sample in step (c) of the procedure recited in steps (a) through (d).

20. A bovine glycoprotein according to claim 17, containing a label selected from the group consisting of radioisotopes, fluorogens, chromophores, enzymes, luminescent substances and other known labels used in immunoassay procedures.

21. The labelled bovine glycoprotein of claim 20 in which the label is $^{125}$I.

22. A radioimmunoassay procedure for determining the quantity of heterophile antibody of human infectious mononucleosis that is present in a test sanple wherein the antigen for said antibody comprises labelled bovine glycoprotein of claim 21.

23. A procedure according to claim 22 in which the radioimmunoassay is of the sandwich type.

24. A procedure according to claim 23 in which the radioimmunoassay is a competition assay.

25. A radioimmunoassay procedure according to claim 24 in which is unlabeled bovine glycoprotein corresponding to the labelled bovine glycoprotein is bound to a solid surface.

* * * * *